US009107699B2

(12) United States Patent
Lauchner et al.

(10) Patent No.: US 9,107,699 B2
(45) Date of Patent: Aug. 18, 2015

(54) BONE TAMP AND METHODS OF USE (71) Applicant: KYPHON SARL, Neuchatel (CH)

(72) Inventors: Craig E. Lauchner, Mountain View, CA (US); Michael A. Smith, San Jose, CA (US)

(73) Assignee: KYPHON SARL, Neuchatel (CH)

( * ) Notice: Subject to any disclaimer, the term of this patent is extended or adjusted under 35 U.S.C. 154(b) by 0 days.

(21) Appl. No.: 14/132,349

(22) Filed: Dec. 18, 2013

(65) Prior Publication Data

US 2014/0107716 A1 Apr. 17, 2014

Related U.S. Application Data (62) Division of application No. 13/098,006, filed on Apr. 29, 2011, now Pat. No. 8,728,081.

(51) Int. Cl.
*A61B 17/56* (2006.01)
*A61B 17/88* (2006.01)

(52) U.S. Cl.
CPC ............. *A61B 17/56* (2013.01); *A61B 17/885* (2013.01); *A61B 17/8852* (2013.01); *A61B 17/8855* (2013.01); *A61B 17/8858* (2013.01); *A61B 2017/564* (2013.01)

(58) Field of Classification Search
CPC ............. A61B 17/56; A61B 2017/564; A61B 17/885; A61B 17/8852; A61B 17/8855; A61B 17/8858
USPC ............. 604/99.01–99.04, 101.01, 604/101.04–101.05, 248, 264, 523; 606/86 R, 191–192, 198
See application file for complete search history.

(56) References Cited

U.S. PATENT DOCUMENTS

| 5,002,558 | A | 3/1991 | Klein et al. | |
|---|---|---|---|---|
| 5,725,535 | A | * 3/1998 | Hegde et al. | 606/108 |
| 5,730,725 | A | 3/1998 | Yoon | |
| 5,919,163 | A | 7/1999 | Glickman | |
| 6,235,043 | B1 | 5/2001 | Reiley et al. | |
| 6,623,505 | B2 | * 9/2003 | Scribner et al. | 606/192 |
| 6,692,484 | B1 | 2/2004 | Karpiel et al. | |
| 7,179,251 | B2 | 2/2007 | Palasis | |
| 7,666,205 | B2 | * 2/2010 | Weikel et al. | 606/192 |

(Continued)

FOREIGN PATENT DOCUMENTS

WO   WO2006034396 A2   3/2006

OTHER PUBLICATIONS

International Search Report issued in International Application No. PCT/US2012/032412, mailed Sep. 28, 2012.

*Primary Examiner* — Larry E Waggle, Jr.
(74) *Attorney, Agent, or Firm* — Sorell Lenna & Schmidt LLP (57) ABSTRACT A system comprises an inflatable bone tamp including a plurality of linearly aligned expandable bodies. The system further comprises an elongated tubular shaft extending through the plurality of linearly aligned expandable bodies. The elongated tubular shaft includes a shaft wall and an interior partition structure. The system further comprises a plurality of channels extending through the shaft, each of the channels formed by a segment of the shaft wall and the interior partition structure and each of the channels in communication with the respective one of the plurality of expandable bodies via openings in the shaft. Each of the expandable bodies is independently inflatable.

20 Claims, 5 Drawing Sheets

(56) References Cited

U.S. PATENT DOCUMENTS

| | | |
|---|---|---|
| 7,708,715 B2 | 5/2010 | Gellman |
| 2004/0068226 A1 | 4/2004 | Brannon |
| 2007/0083224 A1 | 4/2007 | Hively |
| 2007/0225219 A1 | 9/2007 | Boden et al. |
| 2008/0045881 A1 | 2/2008 | Teitelbaum |
| 2008/0140201 A1 | 6/2008 | Stad et al. |
| 2009/0088788 A1* | 4/2009 | Mouw .................. 606/192 |
| 2010/0241178 A1 | 9/2010 | Tilson et al. |
| 2011/0213301 A1 | 9/2011 | Auyoung |

* cited by examiner

BONE TAMP AND METHODS OF USE

This application is a division of U.S. patent application Ser. No. 13/098,006, filed on Apr. 29, 2011, which is expressly incorporated herein by reference, in its entirety.

BACKGROUND

Bone loss is commonly associated with several diseases, including osteolysis, metastatic lesions, and osteoporosis. Though bone loss often refers to the dissolution of bone secondary to a variety of medical conditions, the term osteolysis generally refers to a bone resorption problem common to artificial joint replacements such as hip replacements, knee replacements, and shoulder replacements. Osteolysis often occurs in the bone adjacent to an orthopedic implant, such as a hip or knee implant. As the body attempts to clean the orthopedic implant wear particles from the surrounding bone, an autoimmune reaction may be triggered. This autoimmune reaction causes the resorption of living bone tissue in addition to resorption of the wear particles. This bone resorption forms voids or osteolytic lesions in the bone. Osteolytic lesions are typically soft and spongy, and are unsupportive of orthopedic implants. They may be amorphous and have indeterminate boundaries as viewed on radiographic images. An osteolytic lesion can cause a well-fixed implant to loosen. To treat osteolysis in the area of an implant, it is often necessary to conduct a revision surgery in which the old implant is removed, the lesion is debrided, and a larger revision implant is inserted.

In addition to osteolytic lesions secondary to implant reactions, another common form of osteolytic lesions are "punched out" osteolytic lesions secondary to metastatic cancer. "Punched-out" osteolytic lesions are characteristic of metastatic lung and breast cancers and multiple myeloma.

Both types of osteolytic lesions can trigger a host of serious medical problems in patients, including severe pain, bone fractures, life-threatening electrolyte imbalances, and nerve compression syndromes. One of the treatments for alleviating the symptoms of osteolytic lesions involves clearing the lesion of cellular debris and filling it with biomaterial or bone cement. Because patients with osteolytic lesions are typically older, and often suffer from various other significant health complications, many of these individuals are unable to tolerate invasive surgery. Therefore, in an effort to more effectively and directly treat osteolytic lesions, minimally invasive procedures may be utilized to repair the bone by injecting an appropriate amount of flowable reinforcing material into the osteolytic lesion. Shortly after injection, the filling material hardens, thereby filling the lesion and supporting the bone internally.

In contrast to an open procedure for the same purpose, a minimally invasive, percutaneous procedure will generally be less traumatic to the patient and result in a reduced recovery period. However, minimally invasive procedures present numerous challenges. For example, conventional single balloon catheters used to compact bone and create cavities for reinforcing material are too small for use with the larger osteolytic lesions. Further, conventional single balloon catheters do not allow for versatile control of balloon inflation to accommodate the amorphous nature of osteolytic lesions. Accordingly, there exists a need for instrumentation and techniques that facilitate the more effective and efficient treatment of bone dissolution using minimally invasive procedures.

SUMMARY

The present invention relates to devices and methods for cavity creation in bone with bone lesions, including osteolytic lesions and other areas of bone loss.

In one embodiment, a system comprises an inflatable bone tamp including a plurality of linearly aligned expandable bodies. The system further comprises an elongated tubular shaft extending through the plurality of linearly aligned expandable bodies. The elongated tubular shaft includes a shaft wall and an interior partition structure. The system further comprises a plurality of channels extending through the shaft, each of the channels formed by a segment of the shaft wall and the interior partition structure and each of the channels in communication with the respective one of the plurality of expandable bodies via openings in the shaft. Each of the expandable bodies is independently inflatable.

In another embodiment, a method of creating a cavity in a bone comprises inserting, into a region of the bone with an osteolytic lesion, an inflatable bone tamp. The bone tamp includes a plurality of linearly aligned expandable bodies and an elongated tubular shaft extending through the plurality of expandable bodies. The elongated tubular shaft includes a shaft wall and an interior partition structure. The method further comprises injecting a first amount of inflation medium into a first channel formed by a first segment of the shaft wall and the interior partition structure to inflate a first one of the plurality of expandable bodies. The method further includes injecting a second amount of inflation medium into a second channel formed by a second segment of the shaft wall and the interior partition structure to inflate a second one of the plurality of expandable bodies.

In another embodiment, a system comprises an inflatable bone tamp including first, second, and third linearly aligned expandable bodies. The bone tamp has a length of at least 30 mm. The system further comprises an elongated tubular shaft extending through the first, second, and third expandable bodies. The elongated tubular shaft has an inner lumen and shaft wall. The system further includes first, second, and third channels extending through the shaft, each of the channels in communication with the respective first, second, and third expandable bodies via openings in the shaft wall. Each of the expandable bodies is independently inflatable.

Further aspects, forms, embodiments, objects, features, benefits, and advantages of the present invention shall become apparent from the detailed drawings and descriptions provided herein.

DETAILED DESCRIPTION

The present disclosure relates generally to the field of bone void creation, and more particularly to systems and methods for treating a bone lesions, including osteolytic and metastatic lesions. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein, are contemplated as would normally occur to one skilled in the art to which the disclosure relates.

Figure 1:
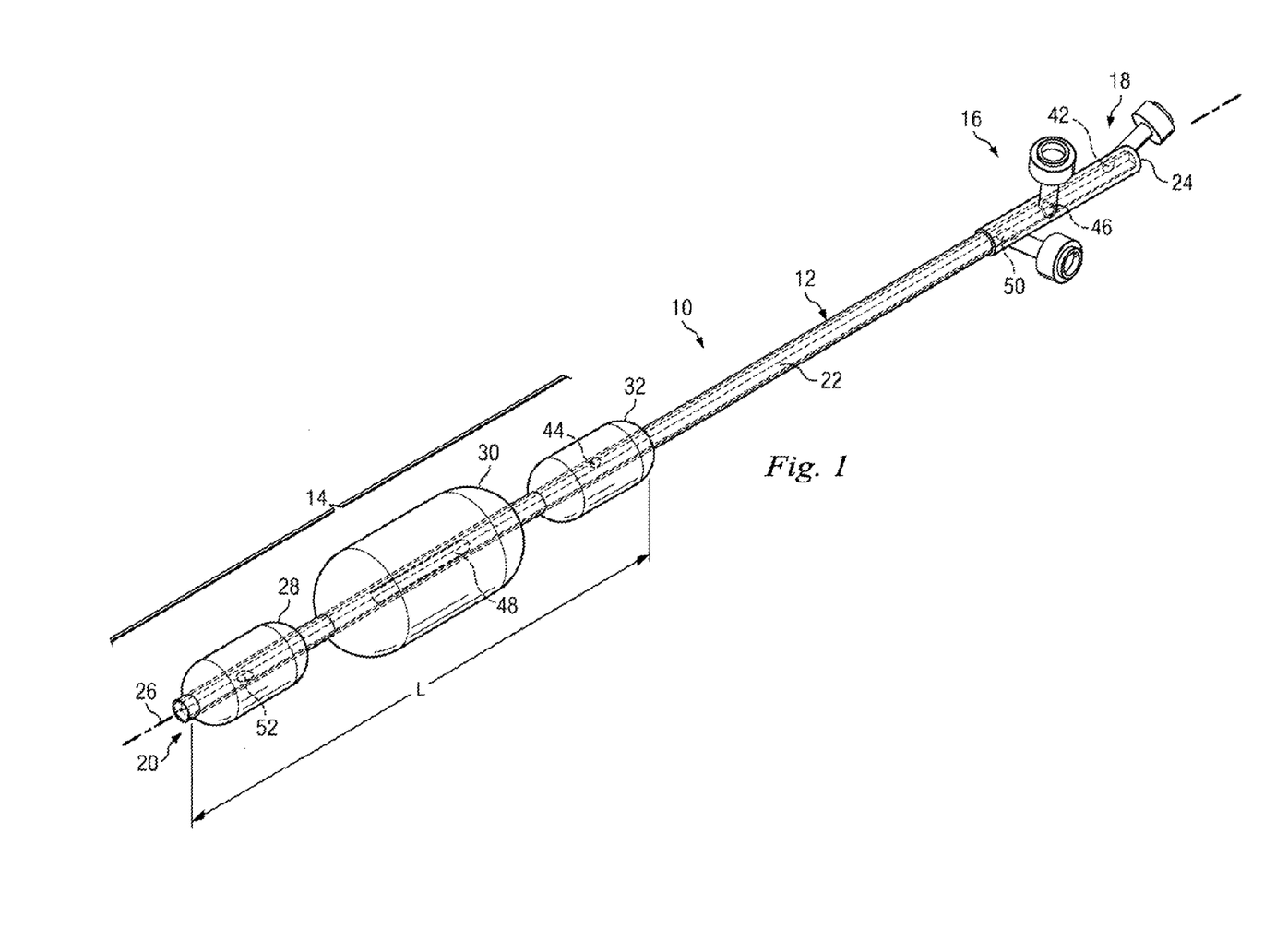
FIG. 1 is a perspective view of a bone treatment system according to one embodiment of this disclosure.

FIG. 1 is a perspective view of a bone treatment system 10 that can be used in a surgical procedure such as the treatment of an osteolytic lesion. The bone treatment system 10 includes an elongated shaft 12, a bone tamp 14, and a connector system 16. The elongated shaft 12 is a generally hollow, cylindrical tube with a proximal end 18 and a distal end 20. The elongated shaft 12 includes an outer wall 22 surrounding a lumen 24. An axis 26 is defined by the elongated shaft 12. The shaft 12 is comprised of a biocompatible material that is more resistant to expansion than the material of the bone tamp 14. Further, the materials for the shaft may be selected to facilitate advancement of the bone tamp 14. The shaft can be constructed, for example, using standard flexible, medical grade plastic materials, like vinyl, nylon, polyethylenes, ionomer, polyurethane, polyether block amide, and polyethylene terephthalate (PET). The shaft can also be fabricated from more rigid materials to impart greater stiffness and thereby aid in its manipulation. More rigid materials that can be used for this purpose include stainless steel, nickel-titanium alloys, and other metal alloys.

The bone tamp 14 includes a plurality of expandable bodies 28, 30, 32 coupled to the distal end 20 of the shaft 12 and linearly aligned along the axis 26. The expandable bodies can be comprised of a flexible and biocompatible material common in medical device applications, including, but not limited to, plastics, polyethylene, mylar, rubber, nylon, polyurethane, latex, metals or composite materials. For example, the expandable body can be formed from a compliant (e.g., latex), semi-compliant (e.g., polyurethane), or non-compliant (e.g., nylon) material. The total length L of the bone tamp 14 is approximately 30 mm. It is understood that in alternative embodiments, the length of the bone tamp may be longer or shorter and the bone tamp may include fewer or more expandable bodies. The size of the balloon tamp and the number of constituent expandable bodies may be chosen based upon the size and configuration of the bone lesion. In some embodiments, the size of the balloon tamp is larger than would be used for vertebral procedures such as kyphoplasty. The expandable bodies may be spaced as close together as possible along the shaft while still allowing for full inflation of the bodies. In alternative embodiments, the bodies may be spaced further apart. In alternative embodiments, the expandable bodies may be clustered, staggered, or may be spaced radially about the shaft.

Figure 3:
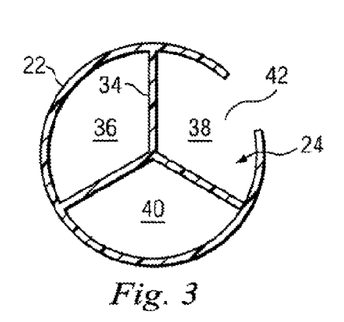
FIGS. 3-5 are cross-sectional views of the proximal end of the bone treatment system of FIG. 1.
Figure 4:
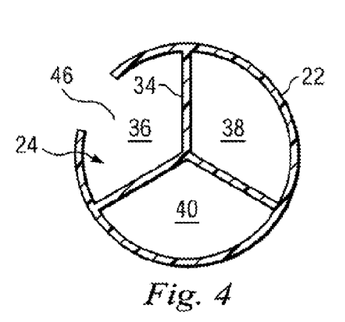
Figure 5:
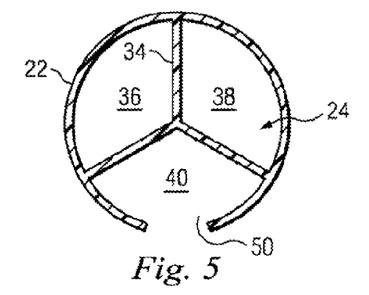

The lumen 24 is configured to carry inflation media or cellular material. As shown in the detailed perspective view of the proximal end of the elongated shaft of FIG. 2 and in the cross-sectional views of the proximal end of the elongated shaft of FIGS. 3-5, the lumen 24 is partitioned so that different sections of the lumen can be used for different purposes. In this embodiment, a Y-shaped partition structure 34 extends through the shaft 12 within the lumen 24. The partition structure 34 divides the lumen 24 into three channels 36, 38, and 40. Each of the channels 36, 38, 40 is defined by a segment of the outer wall 22 and the partition structure 34. Each of the channels 36, 38, 40 has a proximal opening near the proximal end 18 of the elongated shaft 12 and a distal opening near the distal end 20 of the elongated shaft 12. Specifically, as shown in FIG. 3, channel 38 has a proximal opening 42 and a distal opening 44. The distal opening 44 extends through the outer wall 22 of the shaft 12 in a region of the shaft around which the expandable body 32 is coupled. Thus, a flow channel from the proximal opening 42 into the expandable body 32 is created by the channel 38. Similarly, as shown in FIG. 4, channel 36 has a proximal opening 46 and a distal opening 48. The distal opening 48 extends through the outer wall 22 of the shaft 12 in a region of the shaft around which the expandable body 30 is coupled. Thus, a flow channel from the proximal opening 46 into the expandable body 30 is created by the channel 36. Similarly, as shown in FIG. 5, channel 40 has a proximal opening 50 and a distal opening 52. The distal opening 52 extends through the outer wall 22 of the shaft 12 in a region of the shaft around which the expandable body 28 is coupled. Thus, a flow channel from the proximal opening 50 into the expandable body 28 is created by the channel 40.

Although the proximal openings are depicted as generally circular and the distal openings are depicted as generally elongated slots, it is understood that any shape or size of opening in the outer wall 22 may be suitable. Further, the invention is not limited to single proximal and distal openings for each of the channels, rather multiple opening through the outer wall 22 may be suitable. In alternative embodiments, a partition may divide the lumen into fewer or more than three channels. For example, if the bone tamp 14 comprised four expandable bodies, a partition structure may divide the lumen of the shaft into four channels. Alternatively, a partition structure may divide the lumen into four channels with three of the four channels used to create flow channels between proximal openings and a respective expandable body and the fourth channel used to provide a flow channel for aspiration and/or suction. In other alternative embodiments, a radio-frequency instrument may be deployed through one of the channels for ablation of the osteolytic lesion.

Figure 6:
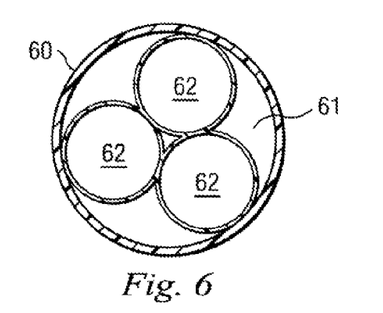
FIG. 6 is a cross-sectional view of a bone treatment system according to another embodiment of this disclosure.

In an alternative embodiment, as shown in FIG. 6, an elongated shaft 60 which is substantially similar to elongated shaft 12 has a lumen 61 through which a plurality of channels 62 extend. Each of the channels 62 is formed by a separate elongated tube, which serves as a partition, and extends between a proximal opening in the shaft 60 to a distal opening in the shaft within a region surrounded by a respective expandable body. It is understood that other partition structures for dividing the lumen of the shaft into channels may be used.

Referring again to FIGS. 1 and 2, the connector system 16 is coupled to the proximal end 18 of the shaft 12. In this embodiment, the connector system 16 includes a connector 66 in communication with the proximal opening 42, a connector 68 in communication with the proximal opening 46, and a connector 70 in communication with the proximal opening 50. Each of the connectors 66, 68, 70 thus allow each of the respective expandable devices 32, 30, 28 to be independently inflated. As depicted, each of the connectors can be a Luer lock connector, but can also be configured in a wide variety of other connector options. For example, the connectors may be configured as a hose barb or a slip fit connector. The connectors 66, 68, 70 are used for receiving inflation material (e.g., saline solution or contrast solution) for inflating the expandable bodies. In alternative embodiments, connectors may also be used for withdrawing cellular matter from an osteolytic lesion and for delivering flowable reinforcement materials, such as bone cement, into the lesion. The connectors 66, 68, 70 provide for the releasable connection of the bone treatment system 10 to a source of flowable material.

Figure 9:
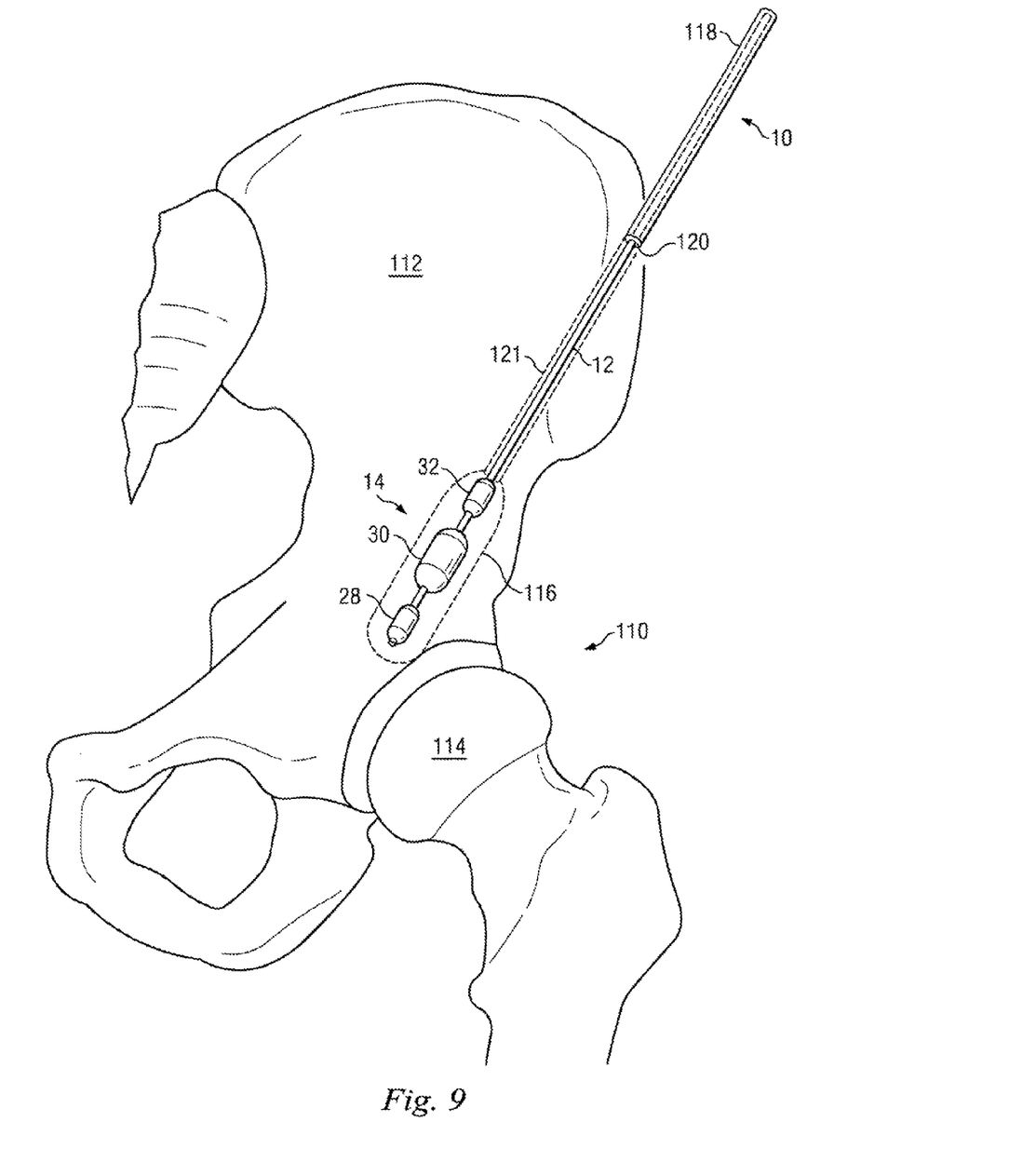
FIG. 9 is a view of the bone treatment system of FIG. 1 in use treating an osteolytic lesion in an ilium.

As shown in FIG. 9, a percutaneous method for using the bone treatment system 10 in a portion of a human hip will be described. An acetabular joint 110 includes an ilium 112 and the head 114 of a femur. Within the ilium 112, a bone lesion 116 has a multi-loculated area of bone loss. It is understood that the systems and methods herein described may be used to treat lesions in other bones such as the femur or the calcaneus.

In this embodiment, the method of use includes inserting a cannula 118 into the ilium 112. In this embodiment, the cannula 118 is an elongated, hollow, cylindrical tube with a lumen 120. The cannula is comprised of a strong, non-reactive, medical grade material, such as stainless steel. In alternative embodiments, the cannula may he any type and size of hollow insertion instrument and may be made from metals or plastics.

The cannula 118 is positioned at an exterior surface of the ilium 112 or shallowly inserted into the ilium using a guide needle and/or dissector. After the cannula 118 is positioned, a drill or other access tool can be used to create a passage 121 through the ilium to the hone lesion 116. The bone tamp 14 carried by the shaft 12 is inserted through the cannula 118, through the passage 121 and into the bone lesion 116. The positioning of the bone tamp and shaft within the bone lesion 116 may be visualized by the physician using visual imaging monitoring techniques such as fluoroscopy. Therefore, in some embodiments, radiopaque markers can be placed at various locations on the bone tamp 14 to facilitate appropriate placement of the bone tamp within the lesion. In other embodiments, the bone tamp 14 may be formed from or can include radiopaque materials. In still other embodiments, the bone tamp 14 or the shaft 12 can include visible indicia such as a marker visible by other imaging modalities such as ultrasound, computed tomography (CT), or magnetic resonance imaging (MRI). In some alternative embodiments, the cannula may be omitted and the bone treatment system 10 may be inserted directly into the bone lesion.

Once the bone tamp 14 is in position, the expandable bodies 28, 30, 32 are independently inflated to compress the walls of the osteolytic lesion 116. Specifically, an inflation medium is conveyed by a fluid dispensing device, such as a syringe, through the connector 66, into the proximal opening 42, through the channel 38 and into the expandable body 32 via the opening 44. The inflation medium causes the expandable body 32 to inflate. Next, using the same or a different fluid dispensing device, an inflation medium is conveyed through the connector 68, into the proximal opening 46, through the channel 36 and into the expandable body 30 via the opening 48. The inflation medium causes the expandable body 30 to inflate. Next, an inflation medium is conveyed through the connector 70, into the proximal opening 50, through the channel 40 and into the expandable body 28 via the opening 52. The inflation medium causes the expandable body 28 to inflate.

The inflation of the expandable bodies causes the surrounding cancellous bone and cellular tissue to become displaced generally outward from the expandable bodies in a controlled manner, forming a compressed bone region or shell. The inflation of the expandable bodies may be monitored fluoroscopically by using radiopaque markers or by using a radiopaque inflation medium. Monitoring allows the physician to selectively and individually inflate the expandable bodies to form an overall bone tamp length and configuration unique to the size and shape of the osteolytic lesion. Because each of the expandable bodies is independently inflatable, the overall shape, size, and configuration of the bone tamp 14 can be individually tailored to for each patient's particular osteolytic lesion. As compared to bone tamps with a single smaller balloon that may require multiple deployments and therefore additional time to fully compress the boundary of the osteolytic lesion, the larger size and versatility of the bone tamp 14 may allow for a single deployment to accomplish the desired bone compression.

It is understood that the provided sequence for inflating the expandable bodies is merely an example and in alternative embodiments the expandable bodies can be inflated in other sequences. For example, in some embodiments it may be desirable to inflate the center expandable body before inflating the outer expandable bodies. Alternatively, it may be desirable to inflate the outer expandable bodies before inflating the center body.

After the shell of compressed bone and other tissue is formed, the inflation medium may be removed from the expandable bodies 28, 30, 32 via the connectors 50, 46, 42, respectively using a fluid suction device such as a syringe. In some embodiments, the inflation medium from one expandable body may be removed before another of the expandable bodies is inflated.

With the expandable bodies 28, 30, 32 deflated, the bone tamp 14 and shaft 12 are withdrawn from the bone through the cannula 118. A flowable bone reinforcement material that sets to a hardened condition, such as bone cement, is injected into the expanded bone lesion 116 and allowed to set to a hardened condition. The shell of compressed bone around the lesion 116 may serve to prevent extravasation of reinforcement material from the bone lesion. The hardened bone filler provides structural support for the bone of the ilium 112 surrounding the bone lesion 116, thereby substantially restoring the structural integrity of the hip. The flowable material can be introduced into the bone lesion by a type of material delivery system known in the art. Suitable flowable reinforcement materials may include graft material or polymer compounds. For example, polymethyl methacrylate (PMMA) compositions such as KYPHON HV-R® Bone Cement or compositions that contain PMMA and hydroxyapatite (HA) such as KYPHON ActivOs™ 10 bone cement offered by Medtronic, Inc. of Minneapolis, Minn. may be suitable.

Figure 2:
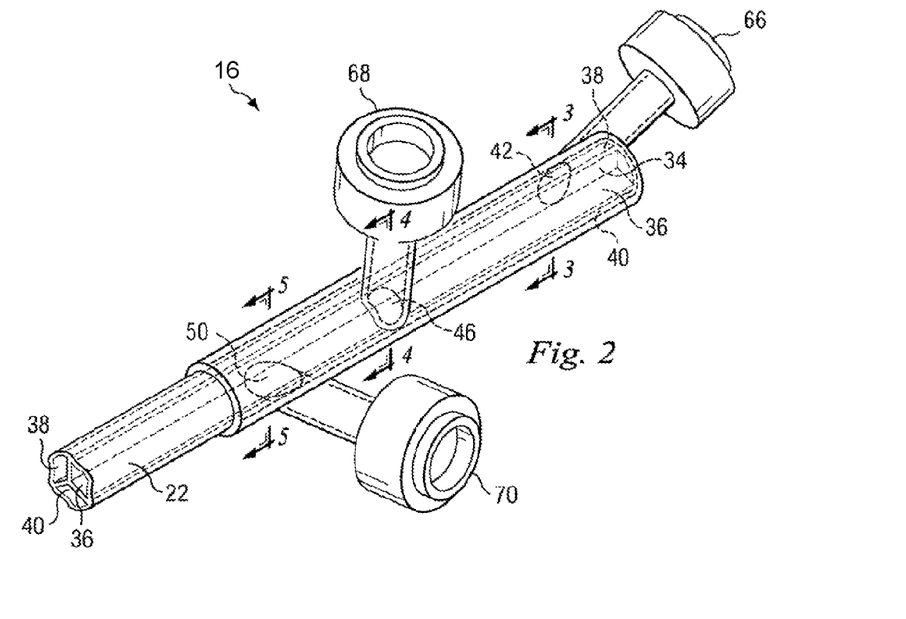
FIG. 2 is a detailed perspective view of a connecter assembly of the embodiment of FIG. 1.

In the embodiment of FIGS. 1 and 2, the connector system 16 has a separate connector associated with each proximal opening and its corresponding channel through the shaft. In alternative embodiments, for example as shown in FIGS. 7 and 8, a single connector is switchable between multiple positions for connecting to different proximal openings to channels within a shaft.

Figure 7:
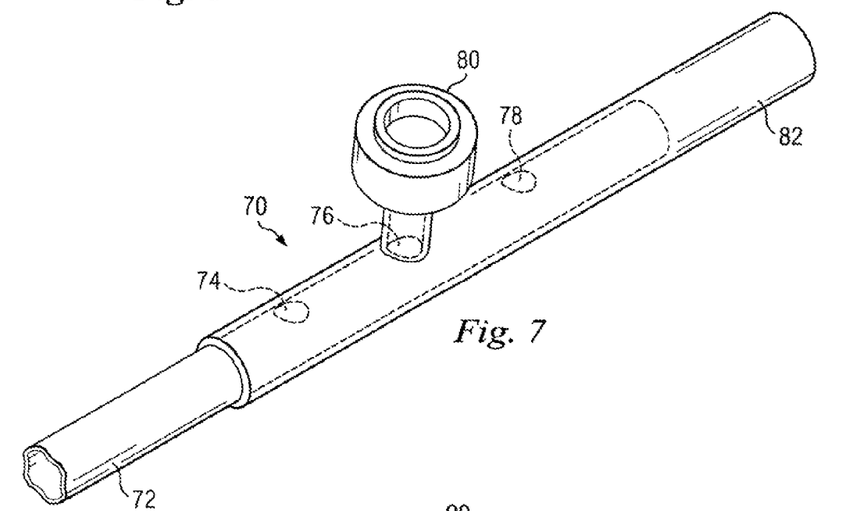
FIG. 7 is a detailed perspective view of a connecter assembly according to another embodiment of this disclosure.

For example, as shown in FIG. 7, a connector system 70 is coupled to an elongated shaft 72. Like the elongated shafts previously described, the elongated shaft 72 has a lumen with a plurality of channels extending therethrough. Each of three channels in the shaft 72 has a respective proximal opening 74, 76, 78 through the wall of the shaft 72. In this embodiment, the proximal openings are linearly aligned, but other arrangements for the proximal openings may be suitable. The connector system 70 includes a connector 80 and a sleeve member 82. The sleeve member 82 is slidably coupled to the shaft 72. The connector system 70 is switchable between a first position in which the connector 80 is in communication with the proximal opening 74, a second position in which the connector 80 is in communication with the proximal opening 76, and a third position in which the connector 80 is in communication with the proximal opening 78. To switch between the first, second, and third positions, the connector system 70 is moved axially along the shaft 72 between the various positions. When the connector 80 is in the first position in communication with the proximal opening 74, the sleeve member 82 seals the openings 76, 78 against inflow of material injected through the connector 80. The connector system 70 may further include a controller (not shown) such as a handle or grip for moving the connector system between positions. Other suitable controllers include rotatable knobs, slider switches, pull tabs, linear actuators, compression grips, and triggers. The controllers may move the connector between multiple preset stops corresponding to the location of the proximal openings.

Figure 8:
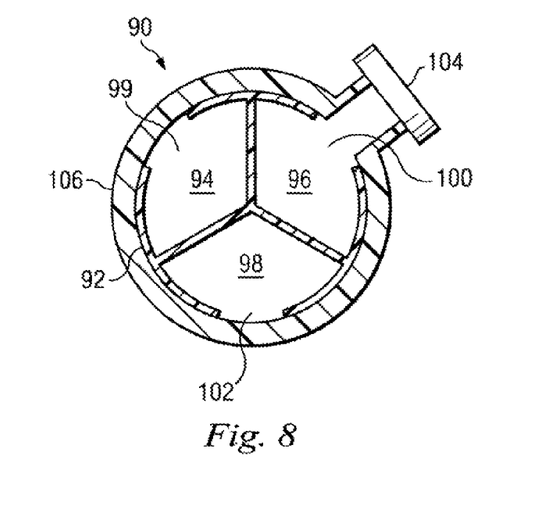
FIG. 8 is a cross-sectional view of a bone treatment system according to another embodiment of this disclosure.

In another embodiment, as shown in FIG. 8, a connector system 90 is coupled to an elongated shaft 92. Like the elongated shafts previously described, the elongated shaft 92 has a lumen with a plurality of channels 94, 96, 98 extending therethrough. Each of channels 94, 96, 98 has a respective proximal opening 99, 100, 102. In this embodiment, the proximal openings are distributed radially around the shaft 92. The connector system 90 includes a connector 104 and a sleeve member 106. The sleeve member 106 is rotatably coupled to the shaft 92. The connector system 90 is switchable between a first position in which the connector 104 is in communication with the proximal opening 99, a second position in which the connector 104 is in communication with the proximal opening 100, and a third position in which the connector 104 is in communication with the proximal opening 102. To switch between the first, second, and third positions, the connector system 90 is rotated about the shaft 92 between the various positions. When the connector 104 is in the second position in communication with the proximal opening 100, the sleeve member 106 seals the openings 99, 102 against inflow of material injected through the connector 104. The connector system 90 may further include a controller (not shown) such as a handle or grip for moving the connector system between positions. Other suitable controllers include rotatable knobs, slider switches, pull tabs, linear actuators, compression grips, and triggers. The controllers may move the connector between multiple preset stops corresponding to the location of the proximal openings.

Figure 10:
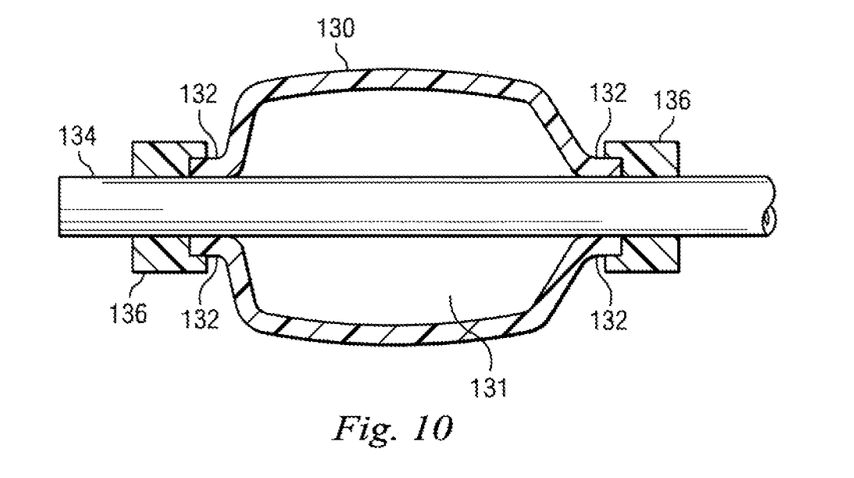
FIGS. 10 and 11 are cross-sectional views of alternative embodiments for connecting an expandable device to a shaft.
Figure 11:
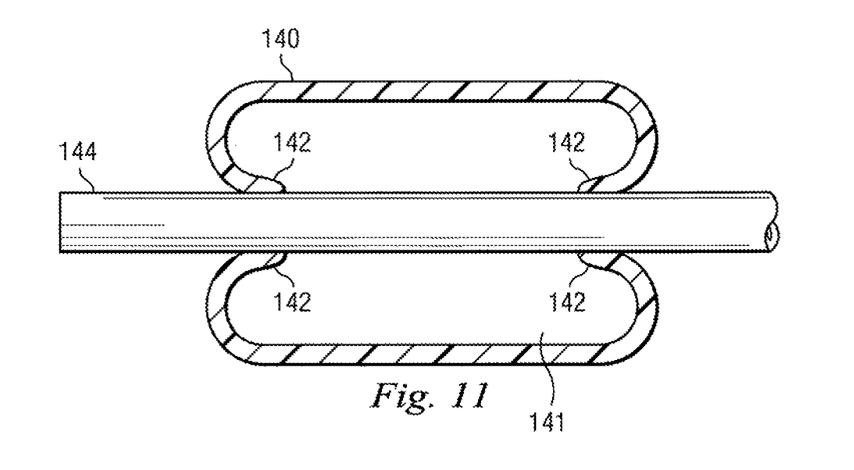

The expandable bodies described above may be connected to the shaft in any of several alternative ways. As shown in FIG. 10, an expandable body 130 includes an expandable region 131 and end portions 132. The end portions 132 extend away from the expandable region 131 and may be attached to a shaft 134 by a heat bond, an adhesive, or a bonding structure 136 such as a collar or a heat shrinkable tubing. As shown in FIG. 11, an expandable body 140 includes an expandable region 141 and end portions 142. The end portions 142 turn inward toward the expandable region and are affixed to a shaft 144 by a heat bond, an adhesive, or any other known bonding technique. The underturned configuration of FIG. 11 may be a particularly beneficial construction for the bone tamp 14 because space along the shaft is not utilized for adhesion of the expandable bodies. With this embodiment, the expandable bodies may be positioned more closely together, and void creation may be more continuous. Further, the underturned configuration may allow an expandable body to be located at a distal most end of the shaft without need to reserve space along the shaft, distal of the expandable body, for attachment of the expandable body to the shaft. The underturned configuration may also assist with removal of the expandable bodies after deflation.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept. In the claims, means-plus-function clauses are intended to cover the structures described herein as performing the recited function and not only structural equivalents, but also equivalent structures.

What is claimed is:

1. A method of creating a cavity in a bone, the method comprising:
   inserting, into a region of the bone with a lesion, an inflatable bone tamp including:
      a plurality of linearly aligned expandable bodies,
      an elongated tubular shaft extending through the plurality of linearly aligned expandable bodies, the elongated tubular shaft including a shaft wall that defines a lumen and an interior partition structure forming a plurality of channels within the lumen, the plurality of channels extending through the shaft, each of the channels formed by a segment of the shaft wall and the interior partition structure and each of the channels in communication with the respective one of the plurality of expandable bodies via openings in the shaft, and
      a sleeve including an inflation port, the sleeve being rotatably coupled to the shaft such that the inflation port is switchable between positions in which the inflation port is in communication with a different one of the channels such that wherein each of the expandable bodies is independently inflatable via the inflation port;
   injecting a first amount of inflation medium into a first channel formed by a first segment of the shaft wall and the interior partition structure to inflate a first one of the plurality of expandable bodies; and
   injecting a second amount of inflation medium into a second channel formed by a second segment of the shaft wall and the interior partition structure to inflate a second one of the plurality of expandable bodies.

2. The method of claim 1 wherein the inflatable bone tamp further comprises an inflation connector coupled to the inflation port.

3. The method of claim 2 further comprising:
   inserting a filling material that sets to a hardened condition into the compacted first and second portion of the bone.

4. The method of claim 1 further comprising:
   compacting a first portion of the bone with the first one of the expandable bodies and compacting a second portion of the bone with the second one of the expandable bodies.

5. The method of claim 1 further comprising:
   injecting a third amount of inflation medium into a third channel formed by a third segment of the shaft wall and the interior partition structure to inflate a third expandable body.

6. The method of claim 1 wherein the inflatable bone tamp has a length of at least 30 mm.

7. The method of claim 1 wherein the step of injecting a first amount of inflation medium includes injecting a first amount of inflation medium through a connector coupled to a port in the first channel.

8. The method of claim 7 further comprising switching the connector to couple to a port in the second channel for injecting the second amount of inflation medium.

9. The method of claim 1 wherein the shaft defines a longitudinal axis and each of the channels includes an aperture configured to be in communication with the inflation port, the apertures each intersecting a single transverse axis that extends perpendicular to the longitudinal axis.

10. The method of claim 1 wherein at least one of the expandable bodies comprises an expandable region and end portions that extend inward toward the expandable region such that an outer surface of a respective expandable member engages an outer surface of the shaft.

11. A method of creating a cavity in a bone, the method comprising:
  inserting, into a region of the bone with a lesion, an inflatable bone tamp including:
    an inflatable bone tamp including first, second, and third linearly aligned expandable bodies, the bone tamp having a length of at least 30 mm,
    an elongated tubular shaft extending through the first, second, and third expandable bodies, the elongated tubular shaft having an inner lumen, an interior partition structure forming a first, second and third channel within the lumen and a shaft wall, the first, second, and third channels extending through the shaft, each of the channels in communication with the respective first, second, and third expandable bodies via openings in the shaft wall, and
    a sleeve including an inflation port, the sleeve being rotatably coupled to the shaft such that the inflation port is switchable between positions in which the inflation port is in communication with a different one of the channels such that each of the expandable bodies is independently inflatable via the inflation port;
  injecting inflation medium into the first channel to inflate the first expandable body; and
  injecting inflation medium into the second channel to inflate the second expandable body.

12. The method of claim 11, further comprising injecting inflation medium into the third channel to inflate the third expandable body.

13. The method of claim 12, further comprising compacting a first portion of the bone with the first expandable body, compacting a second portion of the bone with the second expandable body and compacting a third portion of the bone with the third expandable body.

14. The method of claim 13, further comprising inserting a filling material that sets to a hardened condition into the compacted first, second and third portions of the bone.

15. The method of claim 11, wherein a first amount of inflation medium is injected into the first channel and a second amount of inflation medium is injected into the second channel.

16. The method of claim 11, further comprising compacting a first portion of the bone with the first expandable body and compacting a second portion of the bone with the second expandable body.

17. The method of claim 16, further comprising inserting a filling material that sets to a hardened condition into the compacted first and second portion of the bone.

18. The method of claim 11, wherein the bone is a femur.

19. The method of claim 11, wherein the bone is a calcaneus.

20. The method of claim 11, wherein the bone is an ilium.

* * * * *

UNITED STATES PATENT AND TRADEMARK OFFICE
CERTIFICATE OF CORRECTION

PATENT NO. : 9,107,699 B2
APPLICATION NO. : 14/132349
DATED : August 18, 2015
INVENTOR(S) : Lauchner et al.

Page 1 of 1

It is certified that error appears in the above-identified patent and that said Letters Patent is hereby corrected as shown below:

In the specification

In Column 3, below Line 54, insert -- In one embodiment, the outer expandable bodies 28, 32 may be formed of a compliant material and the central expandable body 30 may be formed of a non-compliant material. In an alternative embodiment, the central expandable body may be formed of a compliant material with the outer expandable bodies formed of a non-compliant material. The size and number of expandable bodies may be selected based upon the size and configuration of the bone lesion in which the bone tamp will be deployed. --, as a new paragraph.

In Column 5, Line 13, delete "may he" and insert -- may be --, therefor.

In Column 5, Line 20, delete "hone" and insert -- bone --, therefor.

Signed and Sealed this
Twenty-second Day of March, 2016

Michelle K. Lee
*Director of the United States Patent and Trademark Office*